United States Patent [19]

O'Connor et al.

[11] Patent Number: 4,857,314
[45] Date of Patent: Aug. 15, 1989

[54] C-REACTIVE PROTEINS IN TREATMENT OF ANIMAL AND HUMAN CANCERS

[75] Inventors: Timothy E. O'Connor; Sherry L. Dupere, both of Williamsville, N.Y.

[73] Assignee: Health Research, Inc., Buffalo, N.Y.

[21] Appl. No.: 886,656

[22] Filed: Jul. 18, 1986

[51] Int. Cl.⁴ ............................................. A61K 37/02
[52] U.S. Cl. ...................................... 424/85.1; 514/2; 514/8; 514/21; 514/885; 514/886; 530/351
[58] Field of Search ................. 514/2, 21, 8, 885, 886; 530/351; 424/85.1

[56] References Cited

FOREIGN PATENT DOCUMENTS 0168214 1/1986 European Pat. Off. .

OTHER PUBLICATIONS

Goldman et al., TBC 262, 1987, pp. 2363-2368.
Old Science 230, 1985, pp. 630-632.
Fransen et al., Nucleic Acid Res., 13(12) 1985, p.4417.
Deodhar et al., Cancer Reserach, vol. 42, 5084-5088 (1982).
Mold et al., J. Exp. Med., vol. 154, 1703-1708 (1981).
Osmand et al., Proc. Natl. Acad. Sci., vol. 74, No. 2, 739-743 (1977).
Whitehead et al., Science, vol. 221, 69-71 (1983).
Oliveira et al., The Journal of Biological Chemistry, vol. 254, No. 2, 489-502 (1979).
Pepys et al., Nature, vol. 273, 168-170 (1978).
Koj, Acute-Phase Reactants, 73-131 (1974).
Gewurz et al., Advances in Internal Medicine, vol. 27, 345-372 (1982).
Kaplan et al., The Journal of Immunology, vol. 112, No. 6, 2135-2147 (1974).
Todd et al., Nature, vol. 313, 803-806 (1985).

Primary Examiner—Howard E. Schain
Assistant Examiner—Garnette D. Draper
Attorney, Agent, or Firm—Birch, Stewart, Kolasch & Birch

[57] ABSTRACT

A pharmaceutical composition comprising an effective antitumor amount of a protein having tumor necrosis activity such as human tumor necrosis factor and an effective immune system stimulating amount of C-Reactive Protein to enhance the antitumor activity of the tumor necrosis factor and a method for treating tumors which comprises administering to a subject having a tumor an effective antitumor amount of a protein having tumor necrosis activity and an effective amount of C-Reactive Protein to stimulate the immune system of the subject thereby enhancing the antitumor activity of the protein.

18 Claims, 3 Drawing Sheets

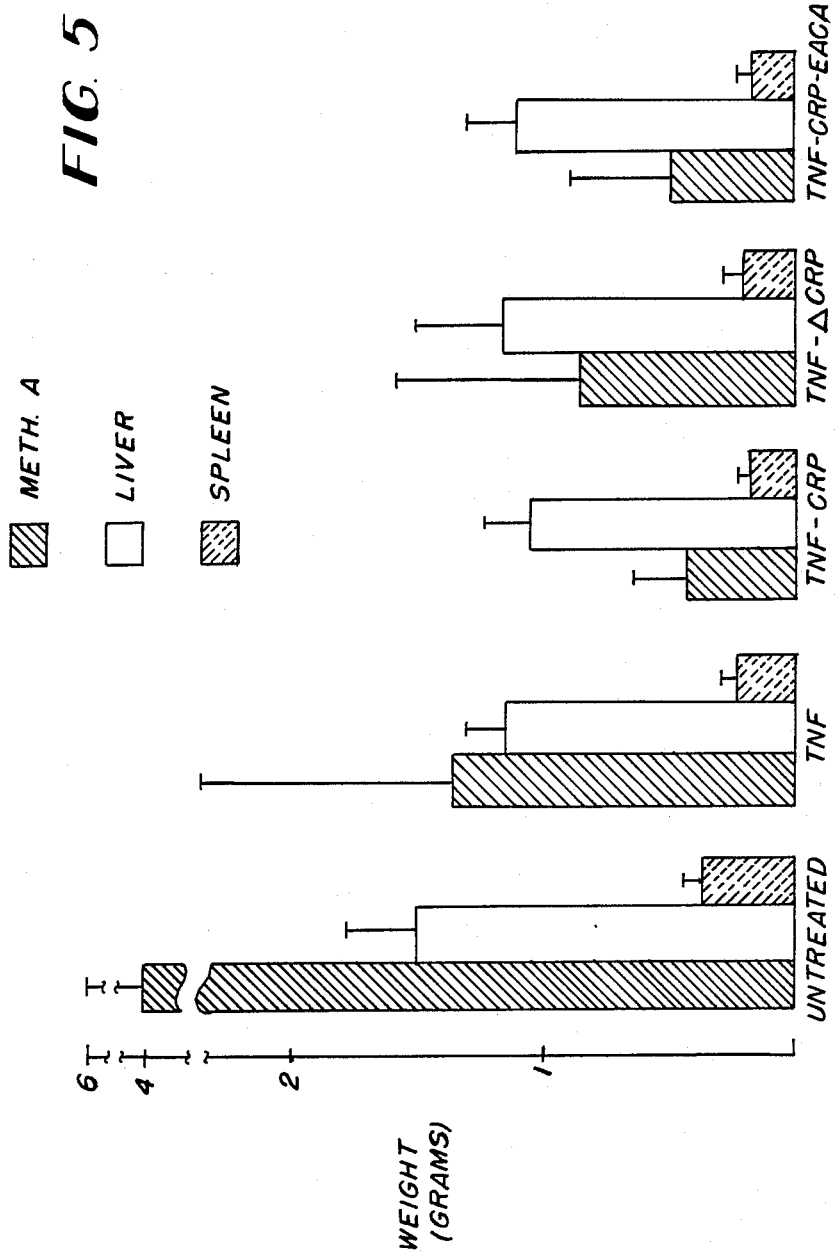

C-REACTIVE PROTEINS IN TREATMENT OF ANIMAL AND HUMAN CANCERS

FIELD OF THE INVENTION

This invention relates to a novel and useful method for the treatment of cancerous tumors in animals and man and more particularly it relates to treatment of animal or human cancers through the administration of C-Reactive Proteins in combination with proteins having tumor necrosis activity such as natural or recombinant Tumor Necrosis Factor.

BACKGROUND OF THE INVENTION

Tumor Necrosis Factors (TNF's) are protein-containing molecules which are excreted by macrophage cells in several species, including man, mouse and rabbit, in response to endotoxin or other appropriate stimuli. TNF's have been shown to be capable of killing cells of several different established animal and human cancer cell lines and of producing ablation of tumors in tumor-bearing animals through production of an hemorrhagic necrosis. Recently, human recombinant TNF, designated Hr-TNF, has been produced and is currently undergoing clinical testing for its effective and safe treatment of human cancers. This invention relates to a further improvement in the efficacy of TNF's (including Hr-TNF) in treatment of cancerous tumors in animals or man through additional administration of a C-Reactive Protein (CRP).

Human CRP (for review see Gewurtz H. et al., Advances in Internal Med. 27, 345-372, 1982) was first detected as a precipitin of bacterial polysaccharides in sera of patients with inflammatory diseases. Human CRP specified by a gene localized on chromosome I (Whitehead, A. S. et al., Science 221, 69-71, 1983) and consists of a single polypeptide chain containing 187 amino acids (Oliveria, E.B. et al., J. Biol. Chem. 254, 489-502, 1979) which is highly homologous to CRP's as isolated from various species including plaice, rabbit and chicken (Pepys, M. B. et al., Nature 273, 169-170, 1978). Recent studies based on the deoxynucleotide sequencing of the cDNA clones and of the genome specifying human CRP suggest that the human CRP is a larger protein than described in the Oliveria reference in that it contains a segment of 19 aminoacids not detected in the Oliveria study that employed aminoacid sequencing (Lei, K. J. et al., J. Biol. Chem. 260, 13377-13383, 1985: Woo P. et al, J. Biol. Chem. 260, 13384-13388, 1985). Chemically the various CRP's are pentraxins and are readily characterized by formation of pentameric pentagonal structures as observed by electron microscopy (Osmond, A.P. et al., Proc. Natl. Acad. Science USA, 74, 739-743, 1977). Human CRP in the presence of calcium ion binds selectively to the phosphorylcholine moiety present in complex bacterial polysaccharides and in disturbed membranes of eukaryotic cells, and in the absence of calcium to polycations such as chromatin. Human CRP is present at less than 10 $\mu$g/ml in normal human serum but can rise over 1,000 fold through production as an acute phase liver protein in response to trauma and inflammation (for review see Koj A "Acute Phase Reactants" in "Structure and Function of Plasma Proteins" Allison A., Ed., pp. 73-131, Plenum Press, New York, 1974). The physiological function of Human CRP is not fully defined. Human CRP has been shown to selectively bind at the site of trauma. Human CRP-C polysaccharide complexes have been shown to bind complement and to activate the classical complement cascade (Kaplan, M. H. and Volanakis, J. E., J. Immunol. 112, 2135-2147, 1974). CRP has also been shown to modulate the physiological activities of platelets, macrophages and NK cells.

Despite these varied physiological activities of human CRP its use in clinical medicine has been restricted to date to its observation as a diagnostic of trauma and inflammation, and particularly as an early diagnostic indicator of cardiac trauma. The use of human or other species CRP's in the therapeutic interventions was unknown except for a single report of protection of mice exposed to Streotococcus pneumoniae with human CRP (Mold, C. et al., J. Exp. Med. 154, 1703-1708, 1984) and a report on inhibition of lung metastases in mice bearing a fibrosarcoma and administered liposomes containing human CRP (Deodhar, S.D. et al., Cancer Res. 42, 5084-5088, 1982).

SUMMARY OF THE INVENTION

The present invention pertains to the finding that combinations of human CRP and Hr-TNF show significantly enhanced antitumor activity as compared to treatment with Hr-TNF alone, even though human CRP administered alone shows only minimal or slight antitumor activity. This invention provides a useful new therapy for animal or human tumors and thus provides a significant improvement over existing modalities of cancer treatments in both veterinary and human medicine.

Therefore, the present invention relates to a pharmaceutical composition comprising an effective tumoricidal amount of a protein having tumor necrosis activity such as tumor necrosis factor and an effective amount of C-Reactive Protein to enhance the tumoricidal activity of the tumor necrosis factor. In addition, the pharmaceutical composition will usually contain a pharmaceutically acceptable carrier or diluent. The pharmaceutical composition may be formulated into a liquid form suitable for intravenous (i.v.), intramuscular (i.m.), intradermal (i.d.) or intraparenteral (i.p.) injection. The pharmaceutically acceptable carrier is preferably a sterile inert material such as sterile physiological saline with an appropriate buffer. The pharmaceutical composition usually comprises 0.01 to 90% total weight of the tumor necrosis factor and the CRP, preferably between 1 and 50% of the TNF and CRP. The TNF and CRP can be present, with respect to each other, in a weight ratio sufficient to allow the CRP to enhance the tumoricidal activity of the TNF. The ratio of the TNF to the CRP is 1 unit of TNF to 0.001-100 $\mu$g of CRP, preferably 1 unit of TNF to 0.01-10 $\mu$g of CRP.

Tumor necrosis factor is a cytokine excreted by macrophages (and perhaps other human cells) which has the capacity to cause hemmorahagic necrosis of a range of cancer tumors and the capacity to kill certain tumor cells in vitro as defined by Carswell, E. A. et al, Proc. Natl. Acad. Science, 72, 3666-3679 (1975). As excreted by the macrophage TNF consists of about 155 amino acid polypeptides whose composition has been defined (Wang, Alice M. et al, Science, 228, 149-154 (1985); Pennica, Diana et al, Nature, 312, 724-729 (1984); and Shirai, T. et al, Nature, 313, 803-806 (1985). A longer precursor molecule is made within the macrophage. Therefore, for the purposes of this application tumor necrosis factor includes, but is not limited to, a protein having about 155 amino acids as reported in European Patent Application Publication Nos. 0158286, 0168214 and 0155549. The term tumor necrosis factor also is intended to cover active fragments or derivatives of the above proteins having the same or similar structure and/or activity.

C-Reactive Proteins of animals or man consist of pentraxin molecules which have the capacity to precipitate bacterial polysaccharides or cellular membranes containing phosphorylcholine receptors and which also have the capacity to form pentameric pentahedral structures detectable by an electron microscope. Human CRP was first described by Tillett, W. S. et al, J. Exp. Med., 52, 561 (1930). Therefore, the term C-Reactive Protein is intended to encompass any of the above-mentioned proteins commonly known as C-Reactive Proteins and any fragments or derivatives of said proteins having the same or similar structure and/or activity.

The present invention also relates to a method for treating patients suffering from tumors. The method comprises the steps of administering to the patient an effective tumoricidal amount of TNF and an effective amount of CRP to enhance the tumoricidal activity of the TNF. The TNF and the CRP can be administered at the same time or one can be administered prior to administration of the other compound. The daily dosage of the TNF is usually between $8 \times 10^4$ to $3 \times 10^6$ units/kg of body weight, preferably $1.5 \times 10^5$ to $3 \times 10^6$ units/kg of body weight. The daily dose of the CRP is usually 0.0024 to 18 mg/kg of body weight, preferably 1.33 to 18 mg/kg of body weight.

The TNF and CRP can be administered by the same route or by different routes of administration. The composition of the present invention has potential utility in the treatment of various types of cancer including the treatment of animal or human sarcomas, breast carcinomas, lung carcinomas, colon carcinomas, and ovarian carcinomas. The composition of the present invention has potential utility as the sole mode of therapy of tumors, but may also be used as an adjunct to other therapies including surgical or radiation ablation of tumors in order to remove either residual tumor masses or metastases of the primary tumor to distant sites (e.g., metastases of colonic carcinomas to liver or lung, or metastases of mammary carcinomas to bone). Since combinations of TNF and CRP are most effective in treatment of early growths of tumors, it is anticipated that such adjunct use of TNF and CRP combinations will be especially useful in preventing secondary or metastatic growths of tumors which presently comprise a major cause of deaths from cancer.

BRIEF DESCRIPTION OF THE DRAWING

FIG. 5 is a bar graph showing the weight of tumors, livers and spleens subjected to various treatment regimens at 22 days post tumor induction with treatments on Day 7.

DETAILED DESCRIPTION OF THE INVENTION

Figure 1:
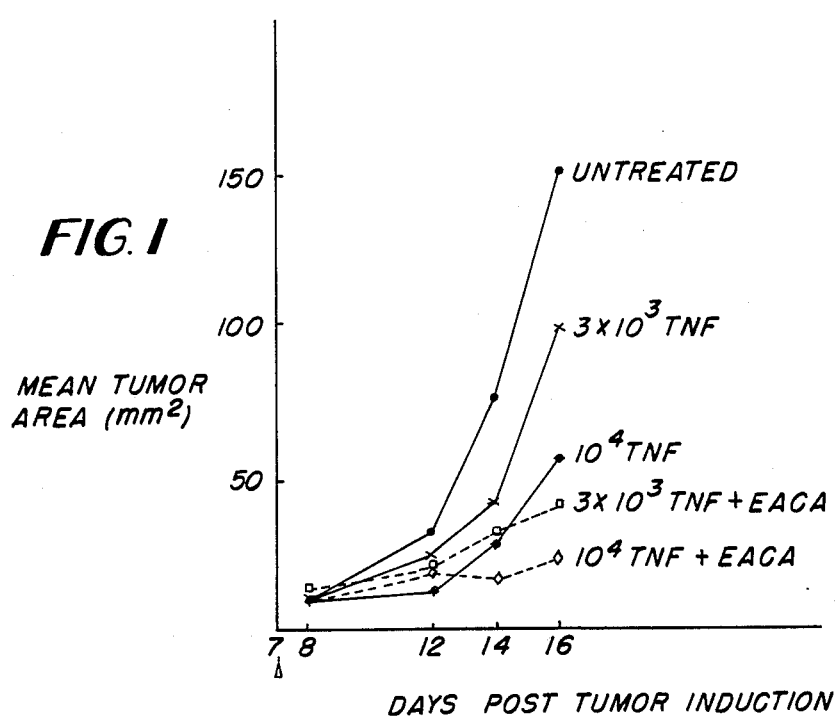
FIG. 1 is a graph showing the antitumor activity against Meth A sarcoma borne by BALB/c mice in response to various compositions containing TNF or TNF and epsilon-aminocaproic acid (EACA), a known inhibitor of various proteases including the exopeptidase which deactivates the C3a component of complement (Hugli, T. E., Vallota, E. and Muller-Eberhard, H. J., J. Biol. Chem. 250: 1472-1498, 1975)

The efficiency of combinations of Hr-TNF and Human CRP in treatment of tumors is shown in the following Examples. In some of the experiments contained in these Examples a non-specific proteinase inhibitor, epsilon aminocaproic acid (EACA), was incorporated in view of its potential as a non-toxic inhibitor of the exopeptidase deactivator of the C3a component of complement. As is noted in the data, the presence of EACA did not significantly increase the toxicity of Hr-TNF or CRP (or combinations). While the presence of EACA produced a modest improvement in antitumor activity, this improvement was not deemed significant statistically at a 95% confidence limit as judged by the Student's t test.

In the following Examples inbred female Balb/c Ros mice at 6-8 weeks of age and 16-18 g body weight were purchased from the West Seneca Mouse Breeding Facility at Roswell Park Memorial Institute. The Meth A Sarcoma was provided by the Asahi Chemical Industry Co., Fuji City, Japan and was passaged weekly as an intraperitoneal ascites tumor for propagation, or passaged intradermally for elicitation of an experimental solid tumor. The ascites passages were periodically reinitiated by intraperitoneal injection of tumor brei to retain the tumorigenic properties of the Meth A sarcoma.

Hr-TNF at $2 \times 10^6$ units per mg protein was provided by Asahi Chemical Industry Co., Fuji City, Japan, as frozen aliquots in PBS, pH 7.4, containing 0.1% gelatin as a stabilizer. For purposes of this application 1 unit of TNF is the amount of TNF which results in cytolysis of 50% of L-M target cells in a standardized methylene blue dye uptake assay.

Hr-TNF suitable for use in the present invention can be prepared and purified by the method disclosed in European Patent Application Publication No. 0158286 or by other methods known in the art. Doses of $3 \times 10^3 - 1 \times 10^6$ units per 0.1 ml per mouse were administered intravenously. EACA was purchased from Sigma Chemical Company, St. Louis, MO, and administered at 1 mg/ml ad libitum in drinking water beginning 24 hours prior to treatment with other agents. Human C-Reactive Protein was purchased from Calbiochem-Behring, San Diego, CA, and was administered intravenously at 250 micrograms per mouse either alone or immediately following administration of Hr-TNF.

Meth A ascites cells, which consistently showed greater than 98% viability based on trypan blue exclusion, were implanted intradermally at $2-3 \times 10^5$ cells per 0.1 ml in the back of the mouse. Palpable tumors developed within one week of inoculation. The largest and smallest diameters of the tumors were measured with a Vernier caliper and the mean tumor area was calculated. In some experiments tumors were surgically removed under anaesthesia at various times within 24 hours of treatment and thin tumor slices were prepared and immediately examined without fixation under an optical microscope. At the termination of experiments (16-21 days) the mice were sacrificed and the tumors, livers, and spleens were excised and weighed. Body weight was monitored throughout the treatment period.

The Student t test was utilized assuming a 95% confidence level ($p<0.05$) as the requirement for significant comparative differences.

Mice bearing palpable tumors at 8–14 days after transplant were examined without further treatment or at 4–10 hours after administration of $1\times 10^4$ U/0.1 ml/mouse of Hr-TNF. Neither untreated nor TNF-treated mice showed gross morbidity changes outside the tumor area, but examination of thin slices of the tumors from Hr-TNF treated mice showed pronounced changes in the tumor vasculature, beginning at about 4 hours post Hr-TNF. treatment. These changes consisted of localized areas of vasculature showing constriction or enlargement and occasional exuding of blood elements within the vasculature. These observations suggested that the tumor-localized hemorrhagic effect of Hr-TNF occurs early as compared to the 20–24 hours that appears necessary for cell killing by Hr-TNF in vitro. The vasculature effects produced by Hr-TNF treatment in vivo appeared to be rendered more pronounced by treatment of the animals with EACA.

EXAMPLE 1

The antitumor activity of intravenous TNF in conjunction with orally-administered EACA was tested. Palpable Meth A sarcoma-bearing mice were treated with $3\times 10^3$ units TNF or $1\times 10^4$ units TNF and compared with these same doses combined with EACA. As illustrated in FIG. 1. TNF was tumoristatic at $1\times 10^4$ units up to day 12. At this time little, if any, significant variation was seen using TNF alone or in combination with EACA. By day 16, an enhancement of antitumor activity at $10^4$ units TNF with EACA was apparent. Nevertheless the statistical significance of this observation is considered borderline ($p<0.1$) in view of the broad standard deviation seen with all EACA. treatments, which may arise from variation in consumption of EACA by each mouse. A similar modest improvement in antitumor effect, of borderline statistical significance, was observed when treatment with $3\times 10^3$ units TNF was compared (FIG. 1) with TNF combined with EACA.

EXAMPLE 2

Figure 2:
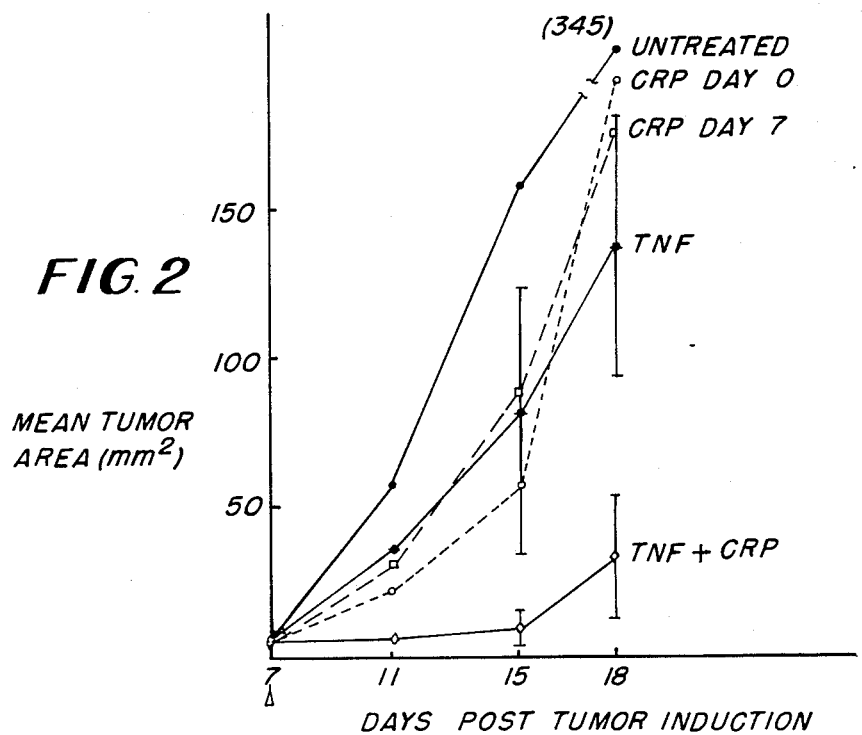
FIGS. 2 and 3 are graphs showing the antitumor activity of various compositions containing TNF and/or CRP.

Tumors were induced by i.d. implantation of $3\times 10^5$ Meth A ascites cells/0.1 ml/mouse. On day 7 (See FIG. 2) the following treatments were administered: TNF at $1\times 10^4$ units/mouse i.v.; CRP at 250 micrograms/mouse i.v.; or combined TNF ($10^4$ U) and CRP (250 micrograms) per mouse i.v. CRP had also been administered to one group of mice (250 μg/mouse) at the time of transplant of the Meth A sarcoma. In this example, the mice administered TNF alone showed decreased antitumor activity as compared to the activity of TNF in Example 1. This result may reflect a higher tumor burden in Example 2, and reflect the sensitivity of TNF efficacy to tumor burden. Nevertheless, the combined effects of TNF and CRP (FIG. 2) show an enhanced antitumor activity as compared to TNF alone ($p<0.001$ at day 18). It should be noted that the tumoristatic activity of the combination is evident for at least 15 days post treatment, long after the biological decay of the single dose of TNF and CRP which is expected to occur within hours and days, respectively. This finding suggests that CRP activates a long-lasting, possible cellular, host defense mechanism. FIG. 2 also illustrates that CRP administered at day 0 or day 7 produced a modest antitumor effect alone that was not significantly different from that produced by TNF alone ($p<0.10$).

EXAMPLE 3

Figure 3:
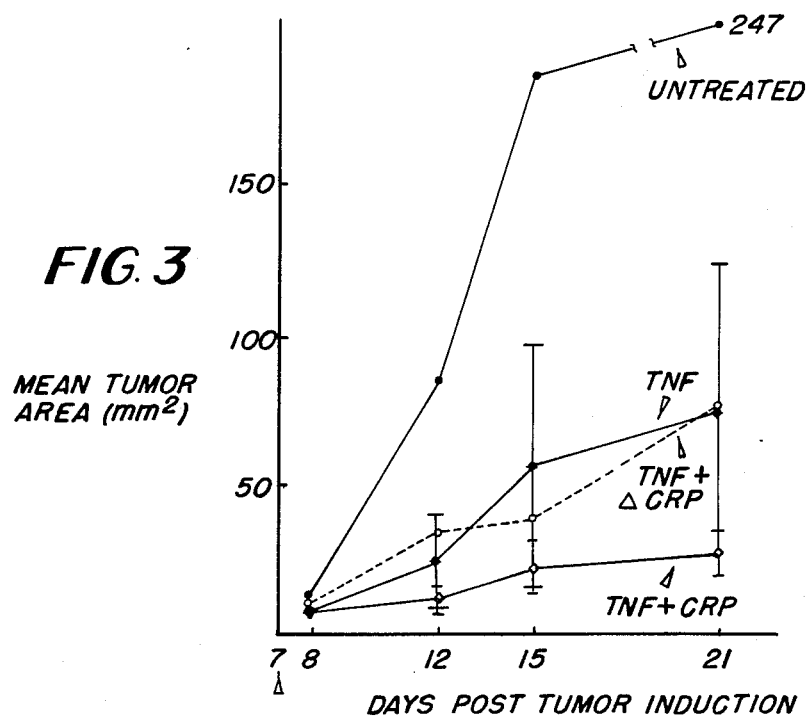

Mice bearing Meth A tumors at seven days post induction by i.d. injection of $3.4\times 10^5$ ascites cells were treated with $1\times 10^4$ units TNF i.v. or this dose of TNF in combination with 250 micrograms CRP or heat-inactivated (63° C., 1 hour) CRP ($\Delta$CRP) and compared with untreated controls. As shown in FIG. 3, the combined TNF-CRP regimen demonstrated maximal antitumor effectiveness. Combined TNF and heat-inactivated CRP was not significantly different from TNF alone ($p<0.5$ at day 15 and day 21), whereas the TNF-CRP (non-inactivated) showed a significant statistical difference to treatment with TNF alone ($p<0.01$).

EXAMPLE 4

Figure 4:
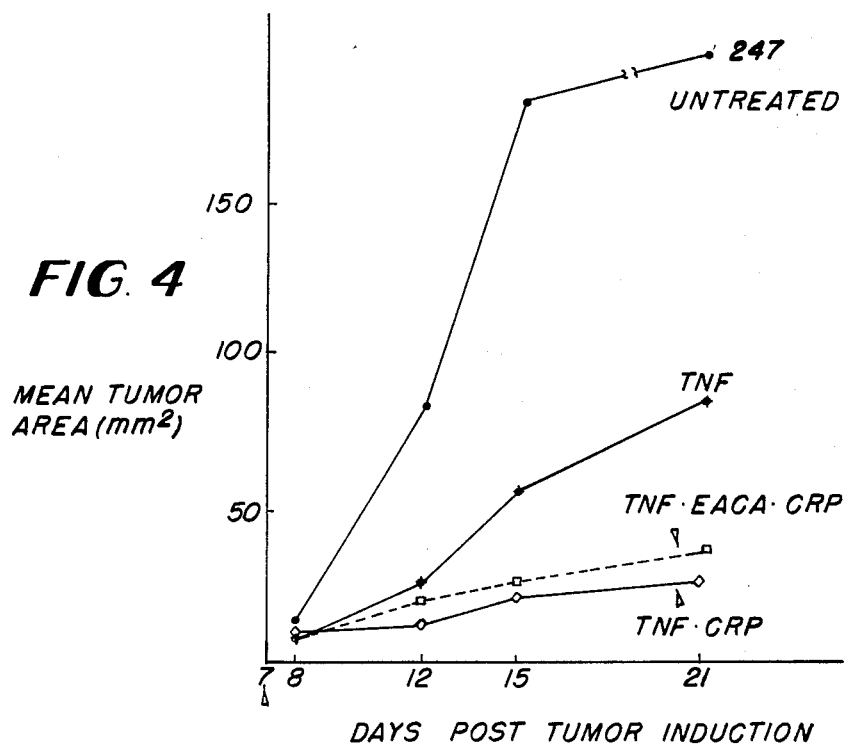
FIG. 4 is a graph showing the antitumor activity of cmpositions containing TNF, TNF and CRP or TNF, EACA and CRP.

Using the experimental conditions of Example 3, tumor-bearing mice were treated with $1\times 10^4$ TNF; $1\times 10^4$ TNF plus 250 micrograms CRP; or $1\times 10^4$ TNF plus 250 micrograms CRP plus EACA on day 7 post tumor transplant. As shown in FIG. 4, statistically significant differences were observed between the untreated mice and mice exposed to any of the treatment regimens. No significant difference was, however, observed in the antitumor activity of the TNF plus CRP regimen versus the TNF plus CRP plus EACA regimen ($p<0.1$), whereas a significant difference was found between the TNF versus TNF plus CRP regimens, and the TNF versus the TNF plus CRP plus EACA regimens ($p<0.01$).

FIG. 5 presents in bar graph form data on excised tumors, livers and spleens in untreated mice and mice exposed to the various treatment regimens at 22 days post tumor induction (treatments on day 7). The data suggests that TNF, CRP and EACA do not alone or in combination contribute to toxicity as judged by spleen or liver weights.

Table I presents a summary of the data from the above Examples and documents the significant enhancement that CRP exerts as an antitumor agent when combined with TNF or mixtures of TNF and EACA.

TABLE 1

| Comparative Treatments at Day 11-14 Post-Rx | | Statistically Significant Difference? |
|---|---|---|
| Untreated | vs. TNF | Yes ($p < .001$) |
| Untreated | vs. CRP-Day 0 | ± ($p = .07$) |
| Untreated | vs. CRP-Day 7 | ± ($p = .08$) |
| TNF | vs. CRP-Day 0 | No ($p < .10$) |
| TNF | vs. CRP-Day 7 | No ($p < .10$) |
| TNF | vs. TNF + EACA | No ($p < .10$) |
| TNF | vs. TNF + CRP | Yes ($p < .001$) |
| TNF + CRP | vs. TNF + CRP + EACA | No ($p < .10$) |
| TNF | vs. TNF + CRP + EACA | Yes ($p < .01$) |

In the experiments reported in Table 1, mice were inoculated with $2-3\times 10^5$ Meth A/Mouse i.d. on day 0, $1\times 10^4$ units TNF/Mouse i.v. on day 7 post tumor induction, 1 mg/ml EACA ad libitum in drinking water at day 6 post tumor induction, and 250 micrograms CRP/Mouse i.v. at day 7.

The Student's t Test was utilized assuming a 95% confidence level ($p<0.05$) as the requirement for significant comparative differences.

USEFULNESS

The mechanisms by which CRP enhances the antitumor activity of TNF are currently unknown. The findings of the present invention, when considered together with the above-noted biological capacities of CRP, suggest that CRP may play a role as a soluble mediator of the non-antigen-dependent immune response (NA-DIR) analogous to the role of immunoglobulin as a soluble mediator in the host antibody-mediated immune response. Whereas antibody (immunoglobulin) shows both molecular diversity and antigenic specificity, he pentraxin CRP molecules show strong evolutionary conservation and apparently achieve their effects through localized binding to exposed phosphorylcholine receptors on deranged cellular membranes with concomitant activation of the complement system and cells such as macrophages. It is of interest that the enhanced anti-tumor effects observed in the present invention involve both a soluble mediator (TNF) derived fromm macrophages and a soluble mediator (CRP) derived from liver cells and that these antitumor effects persist long after the expected residence times of either modulator in plasma.

In current practice of oncology no chemotherapeutic regimen exists which can ablate an established solid tumor in either animals or man when used alone and not as an adjuvant to other modalities of treatment such as surgery or radiation. Hr-TNF is a promising new agent which can produce hemorrhagic necrosis in a number of solid animal tumors. The demonstration that the antitumor activity of this agent can be significantly enhanced by combination therapy with natural human CRP provides promising new approaches to the treatment of animal and human cancers. A feature of interest is that the enhancement of antitumor activity provided by mixtures of TNF and CRP persists for upwards of 13 days following a single inoculation treatment, long after decay of the inoculum components. It should also be noted that the experiments validating the present invention employed both human TNF and CRP in a foreign mouse host system. The preclinical studies comprise a necessary first step in developing preclinical data to ultimately justify clinical human trials on the efficacy and safety of Hr-TNF and CRP in treatment of human cancers. CRP appears to be relatively non-toxic when administered alone and exists naturally in small amounts in the human body. It appears that by administering both CRP and TNF, the CRP may decrease the toxicity of TNF or may lower the amount of TNF needed to exhibit antitumor activity. It can be anticipated that equivalent or superior results will be obtained in these human trials in view of the immunological compatability of Hr-TNF and human CRP with the human host. Such combination therapy would also comprise the first cancer chemotherapy employing solely naturally occurring human products. In the human host, where immunological compatibility would not be a consideration, repeated treatments with combinations of Hr-TNF and human CRP could well lead to total tumor ablation and patient cure.

What is claimed is:

1. A pharmaceutical composition comprising: an effective antitumor amount of human tumor necrosis factor; and an effective immune system stimulating amount of C-Reactive Protein to enhance the antitumor activity of said human tumor necrosis factor.

2. The composition of claim 1, and further comprising epsilon aminocaproic acid.

3. The composition of claim 1, wherein said C-Reactive Protein is human C-Reactive Protein.

4. The composition of claim 1, wherein the ratio of tumor necrosis factor to C-Reactive Protein is 1 unit of tumor necrosis factor to 0.001–100 µg of C-Reactive Protein.

5. A method for treating tumors which comprises: administrating to a subject having a tumor an effective antitumor amount of a protein having a tumor necrosis activity; and an effective amount of C-Reactive Protein to stimulate the immune system of said subject and enhance the antitumor activity of said protein, said tumor being a member selected from the group consisting of breast carcinomas, lung carcinomas, colon carcinomas and ovarian carcinomas.

6. The method of claim 5, wherein said protein is recombinant human tumor necrosis factor.

7. The method of claim 5, wherein said protein is administered in an amount of $8 \times 10^4$ to $3 \times 10^6$ units/kg of body weight.

8. The method of claim 5, wherein said C-Reactive Protein is administered in an amount of 0.0024 to 18 mg/kg of body weight.

9. The method of claim 5, wherein said protein and said C-Reactive Protein are administered at a ratio of 1 unit of said protein to 0.001–100 g of C-Reactive Protein.

10. The method of claim 7, wherein said C-Reactive Protein is administered in an amount of 0.0024 to 18 mg/kg of body weight.

11. The method of claim 6, wherein said human tumor necrosis factor is administered in an amount of $8 \times 10^4$ to $3 \times 10^6$ units/kg of body weight.

12. The method of claim 6, wherein said C-Reactive Protein is administered in an amount of 0.0024 to 18 mg/kg of body weight.

13. The method of claim 11, wherein said C-Reactive Protein is administered in an amount of 0.0024 to 18 mg/kg of body weight.

14. The method of claim 6, wherein said human tumor necrosis factor and C-Reative Protein are administered at a ratio of 1 unit of said human tumor necrosis factor to 0.001–100 µg of C-Reactive Protein.

15. A method for treating tumors which comprises: administering to a subject having a tumor an effective antitumor amount of a protein having a tumor necrosis activity; and an effective amount of C-Reactive Protein to stimulate the immune system of said subject and enhance the antitumor activity of said protein, said tumor being a sarcoma.

16. The method according to claim 5, wherein said tumor is a colon carcinoma.

17. The method according to claim 15, wherein said human tumor necrosis factor and C-reactive Protein are administered at a ratio of 1 unit of said human tumor necrosis factor to 0.001–100 µg of C-Reactive Protein.

18. The method according to claim 16, wherein said human tumor necrosis factor and C-Reactive Protein are administered at a ratio of 1 unit of said human tumor necrosis factor to 0.001–100 µg of C-Reactive Protein.

* * * * *